(12) United States Patent
Whitmarsh et al.

(10) Patent No.: US 12,076,129 B2
(45) Date of Patent: Sep. 3, 2024

(54) APPARATUS AND METHOD FOR DETERMINING AN INDICATION OF BLOOD FLOW

(71) Applicant: Oxford University Innovation Limited, Oxford (GB)

(72) Inventors: Tristan Whitmarsh, Oxford (GB); Piers Milner, Oxford (GB); Ahmed Elzein Mohamed, Oxford (GB)

(73) Assignees: Tristan Whitmarsh, Cambridge (GB); Ahmed Elzein Mohamed, Pontprennau (GB)

( * ) Notice: Subject to any disclaimer, the term of this patent is extended or adjusted under 35 U.S.C. 154(b) by 855 days.

(21) Appl. No.: 17/266,643

(22) PCT Filed: Aug. 7, 2019

(86) PCT No.: PCT/GB2019/052214
§ 371 (c)(1),
(2) Date: Feb. 8, 2021

(87) PCT Pub. No.: WO2020/030908
PCT Pub. Date: Feb. 13, 2020

(65) Prior Publication Data
US 2021/0353163 A1 Nov. 18, 2021

(30) Foreign Application Priority Data

Aug. 10, 2018 (GB) ..................... 1813125
Nov. 1, 2018 (GB) ..................... 1817843

(51) Int. Cl.
*A61B 5/0295* (2006.01)
*A61B 5/00* (2006.01)

(52) U.S. Cl.
CPC .......... *A61B 5/0295* (2013.01); *A61B 5/7246* (2013.01); *A61B 2562/0219* (2013.01);
(Continued)

(58) Field of Classification Search
CPC ....... A61B 5/026; A61B 5/0261; A61B 5/027; A61B 5/053; A61B 5/0535; A61B 5/024; A61B 5/02416
See application file for complete search history.

(56) References Cited

U.S. PATENT DOCUMENTS

2014/0039326 A1 2/2014 Crabtreee et al.
2014/0303460 A1 10/2014 Corley et al.
(Continued)

FOREIGN PATENT DOCUMENTS

EP 3 081 162 A2 10/2016
EP 3074961 A1 10/2016
(Continued)

OTHER PUBLICATIONS

International Search Report & Written Opinion for WO2020/030908 (PCT/GB2019/052214), dated Oct. 9, 2019, pp. 1-9.
(Continued)

*Primary Examiner* — Eric F Winakur
*Assistant Examiner* — Abel Seifu Abegaz
(74) *Attorney, Agent, or Firm* — Thomas |Horstemeyer, LLP

(57) ABSTRACT

The present invention relates to an apparatus and a method for determining an indication of blood flow in a limb. According to an embodiment, the apparatus comprises an orientation sensor, a blood volume (BV) measuring device and a control unit. The orientation sensor is configured to determine an orientation of the limb and output an orientation signal indicative thereof. The blood volume measurement device is configured to measure an indication of blood volume (BV) in the limb and output a BV signal indicative thereof. The control unit is arranged to receive the orientation signal and the BV signal, determine a change in orientation of the limb in dependence on the orientation (Continued)

signal, and correlate the change in orientation with a change in blood volume of the limb determined in dependence on the BV signal.

21 Claims, 7 Drawing Sheets

(52) U.S. Cl.
CPC ................ *A61B 2562/0257* (2013.01); *A61B 2562/0261* (2013.01)

(56) References Cited

U.S. PATENT DOCUMENTS

| | | | |
|---|---|---|---|
| 2016/0278642 A1* | 9/2016 | Vogel | A61B 5/6828 |
| 2017/0000386 A1 | 1/2017 | Salamatian et al. | |
| 2017/0367659 A1* | 12/2017 | Lading | A61B 5/021 |

FOREIGN PATENT DOCUMENTS

| | | |
|---|---|---|
| WO | 2009099315 A1 | 8/2009 |
| WO | 2017005591 A1 | 1/2017 |

OTHER PUBLICATIONS

UK Search Report for GB1813125.0, dated Jan. 31, 2019, pp. 1-5.
Breen Paul P et al: "Hemodynamic monitor for rapid, cost-effective assessment of peripheral vascular function", 2014 36th Annual International Conference of the IEEE Engineering in Medicine and Biology Society, IEEE, Aug. 26, 2014 (Aug. 26, 2014), pp. 4795-4798.
International Preliminary Report on Patentability for WO2020/030908 (PCT/GB2019/052214), dated Feb. 16, 2021, pp. 1-6.

* cited by examiner

APPARATUS AND METHOD FOR DETERMINING AN INDICATION OF BLOOD FLOW

CROSS-REFERENCE TO RELATED APPLICATIONS

This application is the National Stage of International Application No. PCT/GB2019/052214, filed Aug. 7, 2019, which claims priority to GB 1813125.0, filed Aug. 10, 2018 and GB 1817843.4, filed Nov. 1, 2018, which are entirely incorporated herein by reference.

BACKGROUND

Assessment of how well blood can flow through veins has many practical applications in healthcare, in particular the monitoring of a variety of circulatory problems including deep vein thrombosis (DVT). With such problems, a blood clot impedes the flow of blood through the vein. Blood clot detection relies on the accurate measurement of reduced blood flow. Reduced blood flow is difficult to measure in primary care settings, with doctors often relying on checklists of non-specific symptoms.

One way to measure how well the blood flows though the vein is by measuring a venous drainage. Venous drainage can be quantified as a rate of flow out of a limb. For example, in a healthy subject laid in supine position, lifting their leg will cause the blood in the leg to quickly flow out of the veins of the leg. In contrast, in an occluded vein the blood will flow out slowly. The rate of venous drainage can be measured in millilitres per second. However, there are currently problems with measuring venous drainage in this way. Firstly, the machinery to measure the blood volume changes is often bulky, expensive and not easily placed in a doctor's office. Secondly, the interpretation of the resultant data is difficult and requires extensive prior experience. Thirdly, irregular movement of the limb in patients with poor mobility complicates the interpretation of the resultant data, leading to inaccuracies.

It is an object of embodiments of the invention to at least mitigate one or more of the problems of the prior art.

SUMMARY OF THE INVENTION

According to an aspect of the invention, there is provided an apparatus for determining an indication of blood flow in a limb, comprising an orientation sensor for determining an orientation of the limb and outputting an orientation signal indicative thereof, blood volume measurement device for measuring an indication of blood volume (BV) in the limb and outputting a BV signal indicative thereof, a control unit arranged to receive the orientation signal and the BV signal, wherein the control unit is arranged to determine a change in orientation of the limb in dependence on the orientation signal and to correlate the change in orientation with a change in blood volume of the limb determined in dependence on the BV signal.

The control unit may be arranged to determine an indication of venous drainage of the limb in dependence on the correlation of the change in orientation with a change in blood volume of the limb.

The apparatus may comprise a user interface for outputting the indication of venous drainage of the limb.

The control unit is optionally arranged to determine a drainage time of the limb in dependence on the BV signal, indicative of the time at which it takes the blood volume of the limb to drain to a predetermined level.

The control unit may be arranged to determine an indication of venous drainage of the limb in dependence on the drainage time of the limb and the change in orientation of the limb.

Optionally, the indication of venous drainage of the limb is a Venous Drainage Index (VDI).

The control unit may be arranged to determine the VDI as VDI=VDV/VDT, wherein VDV is the change in blood volume of the limb, and VDT is the drainage time of the limb.

The control unit may be arranged to output a signal indicative of the indication of venous drainage.

The control unit is optionally arranged to compare the indication of venous drainage against a predetermined venous drainage threshold and to output a signal in dependence on the comparison.

The control unit may be arranged to determine whether the change in orientation of the limb is within one or more predetermined criteria.

The control unit may be arranged to output an indication if the change in orientation of the limb is outside of the one or more predetermined criteria.

The control unit is optionally arranged to correct the indication of venous drainage if the change in orientation of the limb is outside of the one or more predetermined criteria.

The blood volume measurement device may be a pressure cuff.

The blood volume measurement device may be one of an impedance measurement device, or a strain gauge.

The orientation sensor is optionally one or both of an accelerometer and a gyroscope.

The apparatus may comprise a plurality of orientation sensors each arranged to output an orientation signal and wherein the control means is arranged to, in dependence on the orientation signals, determine an orientation of the limb.

The one or more of the sensors may be arranged to attach to the limb, and one or more of the sensors are arranged to attach to a torso.

The orientation signal may be indicative of the orientation of the limb at predetermined intervals.

The BV signal may be indicative of the blood volume in the limb at predetermined intervals.

The apparatus may be a wearable device.

According to an aspect of the invention, there is provided a computer-implemented method for determining an indication of blood flow in a limb, comprising receiving, from an orientation sensor, an orientation signal indicative of an orientation of the limb, receiving, from a blood volume measuring device, a blood volume (BV) signal indicative of a blood volume in the limb, determining, in dependence on the orientation signal, a change in orientation of the limb, determining, in dependence on the BV signal, a change in blood volume of the limb and correlating the change in orientation with the change in blood volume of the limb.

The method may comprise determining an indication of venous drainage of the limb in dependence on the correlation of the change in orientation with the change in blood volume of the limb.

The method may comprise determining a drainage time of the limb in dependence on the BV signal, indicative of the time at which it takes the blood volume of the limb to drain to a predetermined level.

The method may comprise determining an indication of venous drainage of the limb in dependence on the drainage time of the limb and the change in orientation of the limb.

The indication of the venous drainage of the limb may be a Venous Drainage Index (VDI).

The VDI is optionally determined as VDI=VDV/VDT, wherein VDV is the change in blood volume of the limb, and VDT is the drainage time of the limb.

The method may comprise outputting a signal indicative of the indication of venous drainage.

The method may comprise comparing the indication of venous drainage against a predetermined venous drainage threshold and outputting a signal in dependence on the comparison.

The method may comprise determining whether the change in orientation of the limb is within one or more predetermined criteria.

The method may comprise outputting an indication if the change in orientation of the limb is outside of the one or more predetermined criteria.

The method may comprise correcting the indication of venous drainage if the change in orientation of the limb is outside of the one or more predetermined criteria.

The orientation signal may be indicative of the orientation of the limb at predetermined intervals.

The BV signal may be indicative of the blood volume in the limb at predetermined intervals.

According to an aspect of the invention, there is provided a computer software which when executed by a computer, is arranged to perform a method according to an aspect of the invention.

The computer software may be stored on a computer readable medium. The computer readable medium may be non-transitory.

BRIEF DESCRIPTION OF THE DRAWINGS

Embodiments of the invention will now be described by way of example only, with reference to the accompanying figures, in which.

DETAILED DESCRIPTION OF EMBODIMENTS OF THE INVENTION

Figure 1:
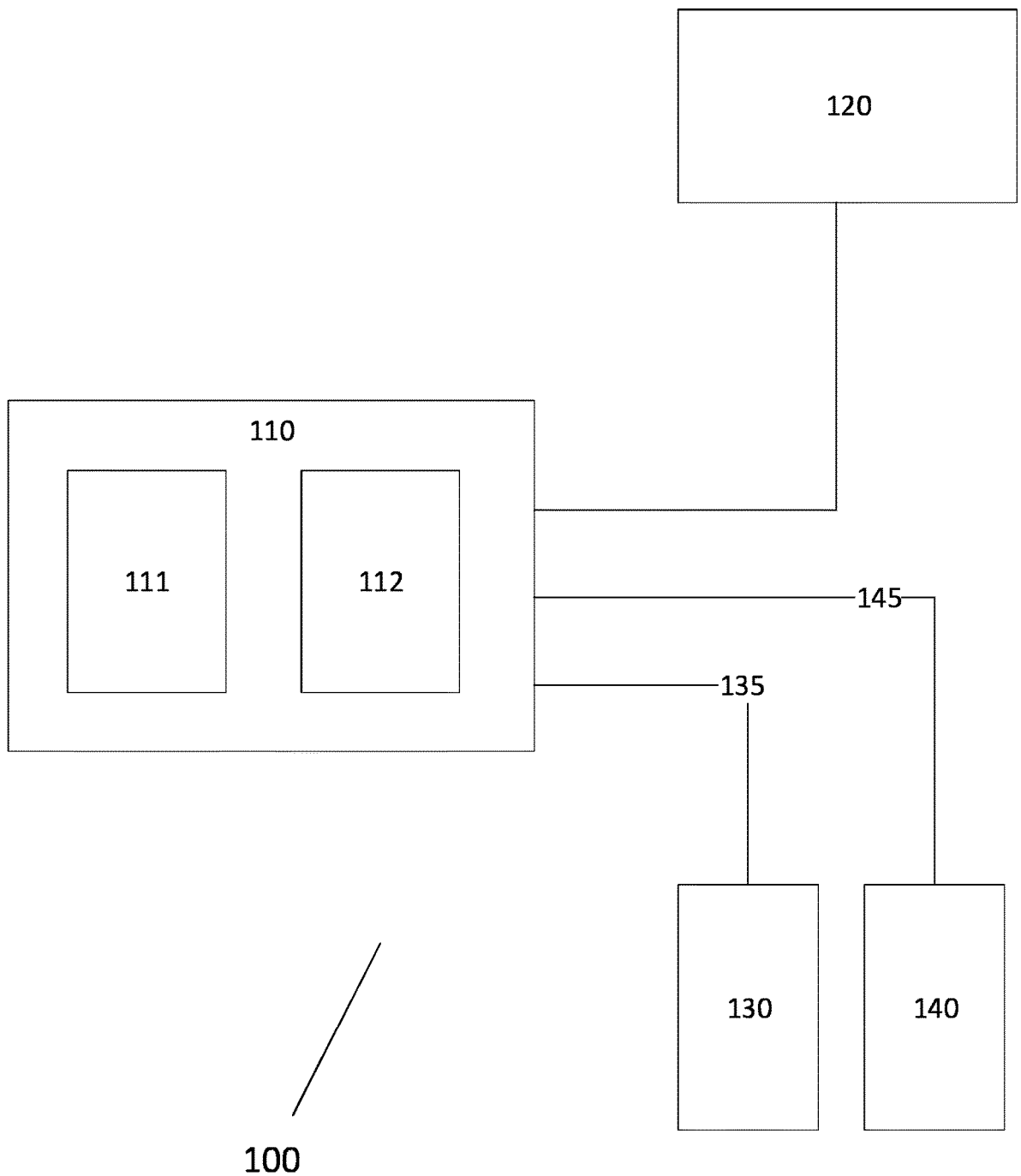
FIG. 1 shows a schematic illustration of an apparatus according to an embodiment of the invention.

FIG. 1 shows a schematic illustration of an apparatus 100 according to an embodiment of the invention. Embodiments of the apparatus 100 may be used to determine an indication of blood flow in a limb, for example to determine an indication of venous drainage of a limb. Embodiments will be described where the limb is a leg of a subject, although it will be appreciated that this is merely illustrative. The apparatus 100 is envisaged to be suitable for use with other limbs, such as arms.

The illustrated embodiment of the apparatus 100 comprises a control unit 110, a user interface 120, an orientation sensor 130 and a blood volume measurement device 140.

The orientation sensor 130 is arranged to determine an orientation of the limb i.e. the leg. The orientation sensor 130 may be, in some embodiments, an accelerometer or a gyroscope, however the orientation sensor may be any device capable of measuring orientation of the limb. The orientation sensor 130 may be arranged as a wearable device such that it is attachable to a body part, for example to the leg. In some embodiments orientation may be understood to mean an inclination of the limb.

In some embodiments of the invention, the orientation sensor 130 may be a plurality of orientation sensors. Each orientation sensor may be attachable to a respective body part i.e. part of a limb i.e. upper and lower leg parts or upper and lower arm parts, or to a respective location on the same body part. In some embodiments, each orientation sensor may be arranged to attach to a respective location along the length of the leg. Advantageously, utilising more than one orientation sensor 130 in this way may provide a more accurate indication of the orientation of the limb or portions thereof. If the leg is bent, for example, the upper and lower legs may not have a consistent orientation and so placing orientation sensors at a plurality of locations along the length of the leg are likely to provide a more accurate indication of the leg's orientation.

Optionally, one or more of the orientation sensors 130 may be arranged to be attachable to a different body part than the limb, for example to a torso of the subject. In this embodiment the plurality of orientation sensors may be utilised to measure relative orientation of the limb to the torso. Measuring the relative orientation of the leg to the torso may be advantageous in allowing posture correction when determining a blood flow in the leg, as will be explained.

Each orientation sensor 130 is arranged to output an orientation signal 135 indicative of the orientation of the body part or portion of the body part to which it is attachable. For example, if the apparatus 100 comprises only one orientation sensor 130 attachable to the limb, the orientation sensor 130 is arranged to output the orientation signal 135 indicative of the orientation of the limb. In an embodiment comprising a plurality of orientation sensors, each orientation sensor 130 may be arranged to output a respective orientation signal 135. The one or more orientation signals 135 are received by the control unit 110.

In a described embodiment the orientation signal 135 comprises data indicative of the orientation of the limb. The data may be associated with time information indicative of a measurement time, such as a timestamp indicative of the time at which the orientation was measured. However, other implementations can be envisaged, for example where the orientation signal is an analogue signal such as a voltage indicative of the orientation. The orientation signal indicates the orientation of the limb over time.

Figure 6:
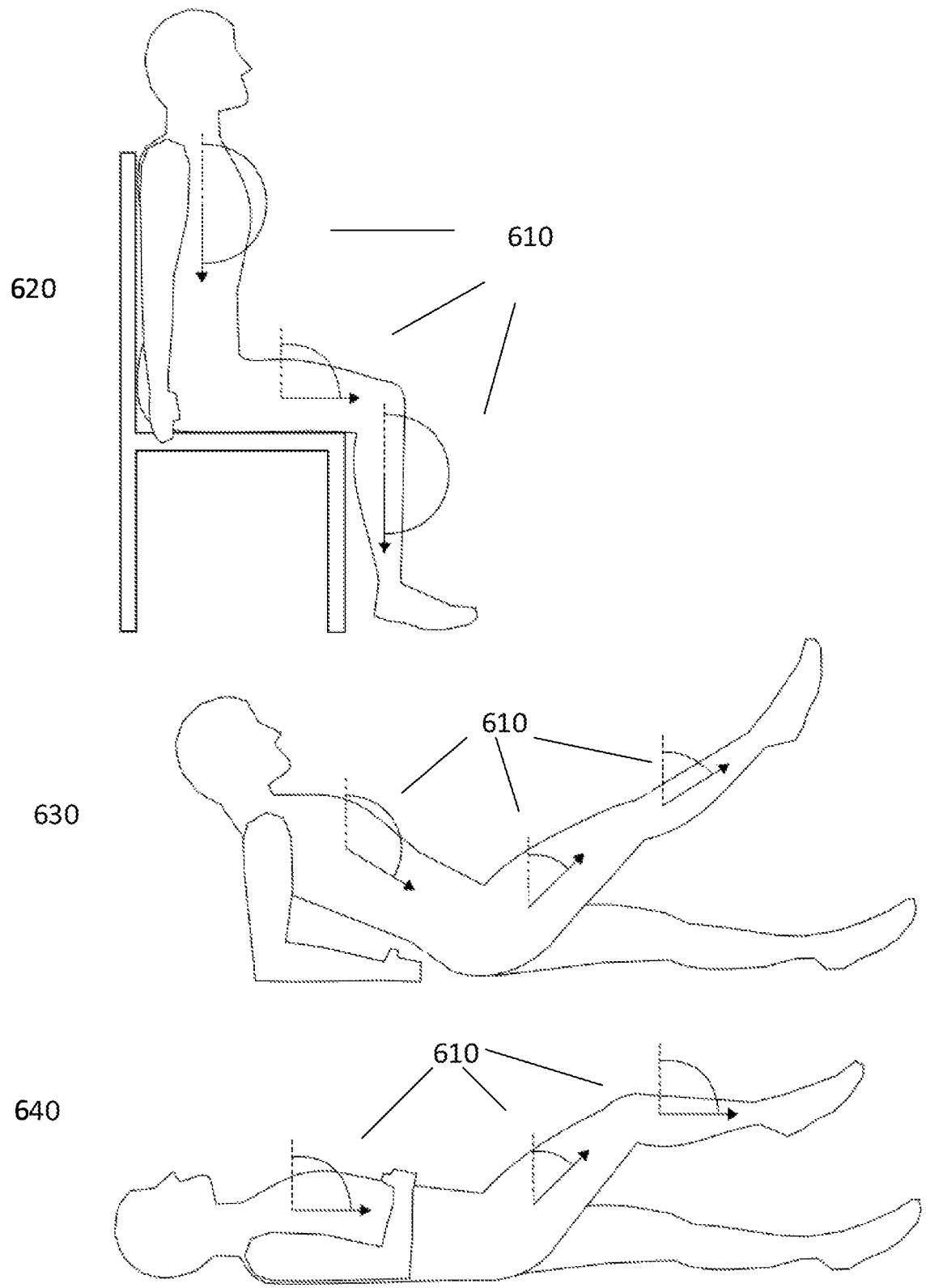
FIG. 6 shows an example configuration of orientation sensors according to an embodiment of the invention.
Figure 7:
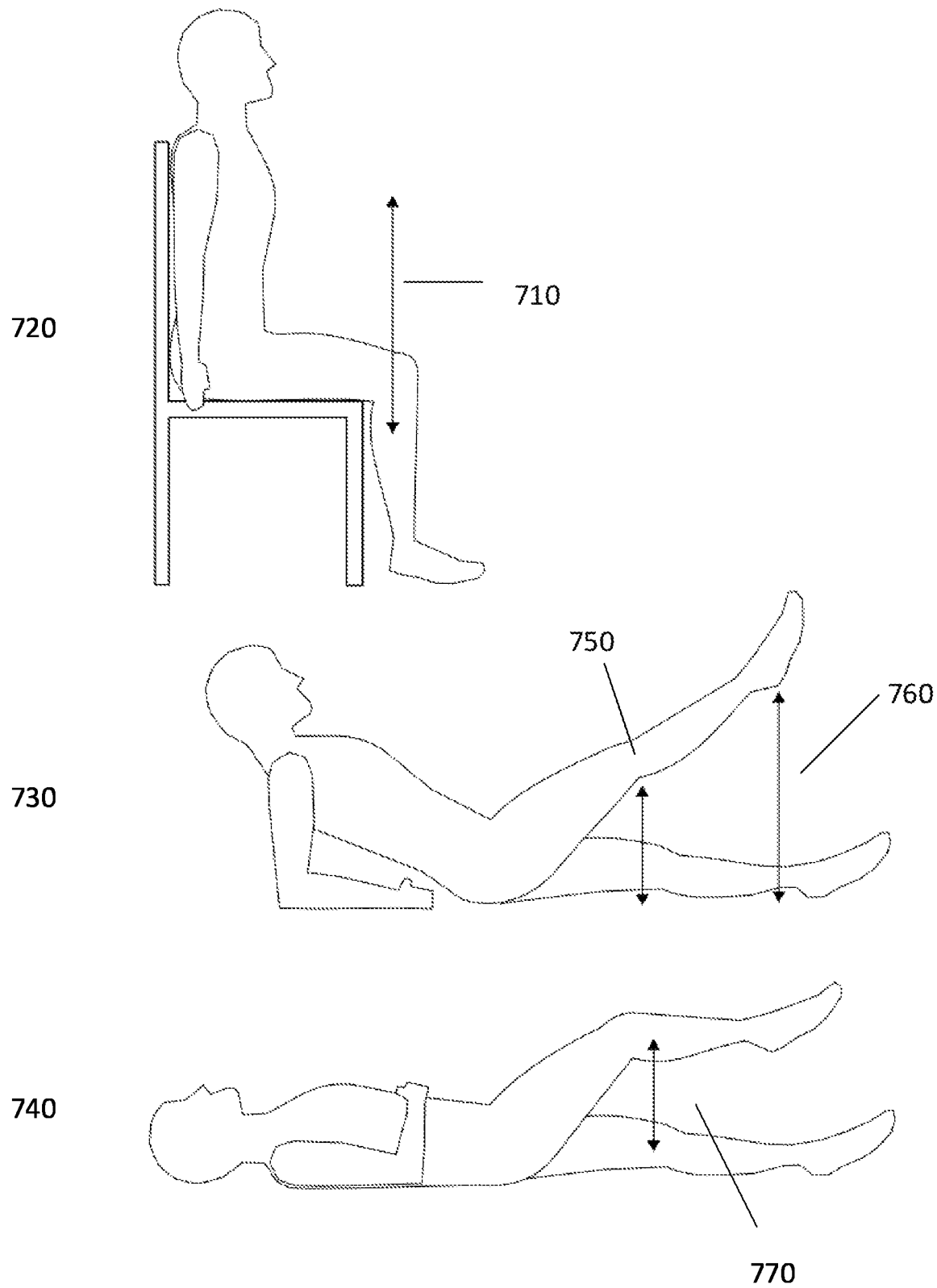
FIG. 7 shows an example configuration of orientation sensors according to an embodiment of the invention.

Illustrative examples of an arrangement of orientation sensors 130 to determine orientation are shown in FIGS. 6 and 7.

As described above, embodiments of the present invention comprise an orientation sensor for determining the orientation of the limb and outputting an orientation signal indicative thereof. It will be understood that the orientation of the limb may mean an orientation or position of the limb with respect to a reference, for example a reference plane or location.

For example, the orientation of the limb with respect to a reference may be an angle of the limb with respect to a reference plane. That is an angle bisected between at least a portion of the limb and the reference plane. As previously mentioned each orientation sensor may be an accelerometer or gyroscope suitable for determining orientation with respect to a reference plane.

The orientation of the limb may mean the relative height or distance of at least a portion of the limb from an object, such as a reference surface, or other body part. Each orientation sensor may then be any device suitable for determining the height or the distance from a reference location.

FIG. 6 illustrates an example wherein an apparatus according to an embodiment of the invention uses a plurality of orientation sensors 610. FIG. 6 illustrates three orientations of the body 620, 630 and 640. In this example the orientation sensors 610 are each attached, in use, to the subject's leg and body. In the example, the orientation sensors 610 are attached, respectively, to the subject's lower leg, upper leg and torso of the body. It will be appreciated that in other examples only one orientation sensor may be attached to the subject's limb, such as the leg, or one or more further orientation sensors may be attached at one or more further locations on the body. Each orientation sensor 610 is arranged to determine an orientation of a respective body part by measuring the relative angle of the body part to which they are attachable, as illustrated in FIG. 6. The orientation signal 135 output from each orientation sensor 610 may be used to determine a relative orientation of two or more of the body parts. For example, each orientation signal 135 may be used to determine the relative orientation between the upper and lower leg, or between the leg and the torso. In some embodiments, the reference plane may be determined with respect to gravity, as illustrated in FIG. 6 where the reference plane may be a vertical plane. However, in other embodiments the reference plane may be another plane such as a horizontal plane.

FIG. 7 illustrates another example. As mentioned, the orientation of the limb may mean the relative height or distance from an object or body part, and each orientation sensor may be any device suitable for determining a height or distance from a reference location. For example, the reference location may be the ground, or a different body part. Each orientation sensor may be, for example, any device capable of transmitting and receiving reflected radiation. Some examples of such orientation sensors may utilise sound radiation, for example an ultrasonic range finder. Other examples may utilise EM radiation, for example an optical device such as a laser distance meter. As mentioned each orientation sensor may be attached in use to a different body part or location on the body part, for example a subject's limbs or torso. Each orientation sensor may then be configured to determine a relative height or distance from the body part to which it is attachable to the reference location. FIG. 7 illustrates three orientations of the body 720, 730 and 740 analogous to those illustrated in FIG. 6. FIG. 7 further illustrates an example selection of heights 710, 750, 760 and 770 that each orientation sensor may be arranged to determine. Each orientation sensor may be arranged to determine one or more of a distance 750 from an upper leg to the ground, a distance 760 of a lower leg to the ground, a distance 770 from a first leg to a second leg, and a height 710 from a location on the leg to a heart of the body. Different distances or heights may also be determined, for example from the torso to the ground.

It will be appreciated that heights 710, 750, 760 and 770 can indicate the orientation of the limb in a comparable level of detail to the relative angles illustrated in FIG. 6. Furthermore, in some embodiments, each orientation sensor 130 may be arranged to determine a combination of a relative angle and a height or distance from a reference location to ensure a high level of accuracy in determining the orientation of the limb.

The apparatus 100 comprises a blood volume (BV) measurement device 140 for measuring an indication of blood volume, BV, in the limb. In some embodiments, the BV measurement device 140 is a wearable device. The BV measurement device 140 may comprise any device from which blood volume may be inferred or estimated. For example, the BV measurement device may comprise one or a combination of a pressure cuff, an impedance measurement device, or a strain gauge, although further alternatives can be envisaged.

In some embodiments, the BV measurement device 140, for example a pressure cuff, may measure an indication of blood pressure. Advantageously, blood pressure may be accurately related to the BV by a calibration of the device. For example, the calibration may comprise adding or removing a known quantity of air and measuring the change in pressure. In some embodiments the BV measurement device 140 may comprise a pump for use in the calibration of the device. The pump may be configured to inject a known volume of air or other fluid into the BV measurement device 140, and the BV measurement device 140 may be configured to store or output calibration data indicative of a relationship between pressure and volume. Advantageously, a change in blood volume (BV) may then be accurately determined by the BV measurement device 140 by converting a change in blood pressure reading to a change in blood volume (BV) using the calibration data.

In some embodiments, the BV measurement device 140 is configured to automatically perform the calibration prior to measuring an indication of blood pressure. For example the BV measurement device 140 may be configured to automatically perform the calibration when it is switched on or receives an indication that it has been attached to a user.

The BV measurement device 140 is further configured to output a BV signal 145 indicative of the BV in the limb. In a described embodiment the BV signal comprises data indicative of blood volume and association time information indicative of a measurement time. The time information may be an associated timestamp indicative of the time at which the blood volume was measured. However, other implementations can be envisaged. The BV signal 145 is received by the control unit 110.

The apparatus 100 comprises a control unit 110. The control unit 110 may be operable to control aspects of the apparatus 100 and to record measured data as will be explained. The control unit 110 may comprise a memory 112, and a processor 111 operable to execute computer readable instructions which may be stored in the memory 112. The control unit may perform operations, such as a method according to an embodiment of the invention, on data stored in the memory 112 as will be explained. The control unit 110 may further comprise an input/output (I/O) device, such as circuitry, to enable communicate data to/from external devices. The I/O device may be a wired or wireless I/O device. The control unit 110 may be connectable to a wireless network. The control unit 110 may be controlled in part by a user, for example via a user interface 120. The control unit 110 may also be controlled in part by software stored on memory 112, executable by processor 111.

The control unit 110 may be arranged to receive the orientation signal and the BV signal from the orientation sensor 130 and the BV measurement device 140 respectively. In some embodiments, the orientation sensor 130 and the BV measurement device 140 are communicable with the control unit 110 via the I/O circuitry, which may be for example a USB connection. In other embodiments, the orientation sensor 130 and the BV measurement device 140 may be connectable to the control unit 110 wirelessly, for example via a wireless network such as Bluetooth® although it will be appreciated that other protocols may be used. The control unit 110 may be arranged to store the data corresponding to the BV signal and the orientation signal in the memory 112. The processor 111 may be configured to execute the computer-readable instructions to perform analysis on the stored orientation signal and the stored BV signal, as will be explained with reference to FIGS. 2 to 5. This analysis may be carried out in real time as the signals are received, or after sufficient data has been received.

In some embodiments, the control unit 110 is configured to determine a change in orientation of the limb in dependence on the orientation signal and determine a change in blood volume of the limb in dependence on the BV signal. The control unit 110 may be further arranged to determine a venous drainage of the limb, as will be explained.

The control unit 110 may be communicable with the user interface 120, as has been mentioned. The user interface 120 may comprise, for example, one or both of a display device and an input device. For example, the user interface 120 may comprise a display screen and a keyboard. The user interface 120 may in some embodiments be an integrated device such as a touch-sensitive display device. The user interface 120 may be an external device such as a mobile phone, portable computer or tablet. The user interface 120 may be integrated with the control means 110, or they may be communicable over a wireless or wired network. The user interface 120 may be arranged to receive a user input for controlling one or more aspects of the apparatus 100. The user interface 120 may also be arranged to receive data from the control unit 110 and to display an indication of the data to a user. For example, the data may be indicative of one or more of the blood volume of the limb, the orientation of the limb, or the venous drainage of the limb, as will be explained.

Figure 2:
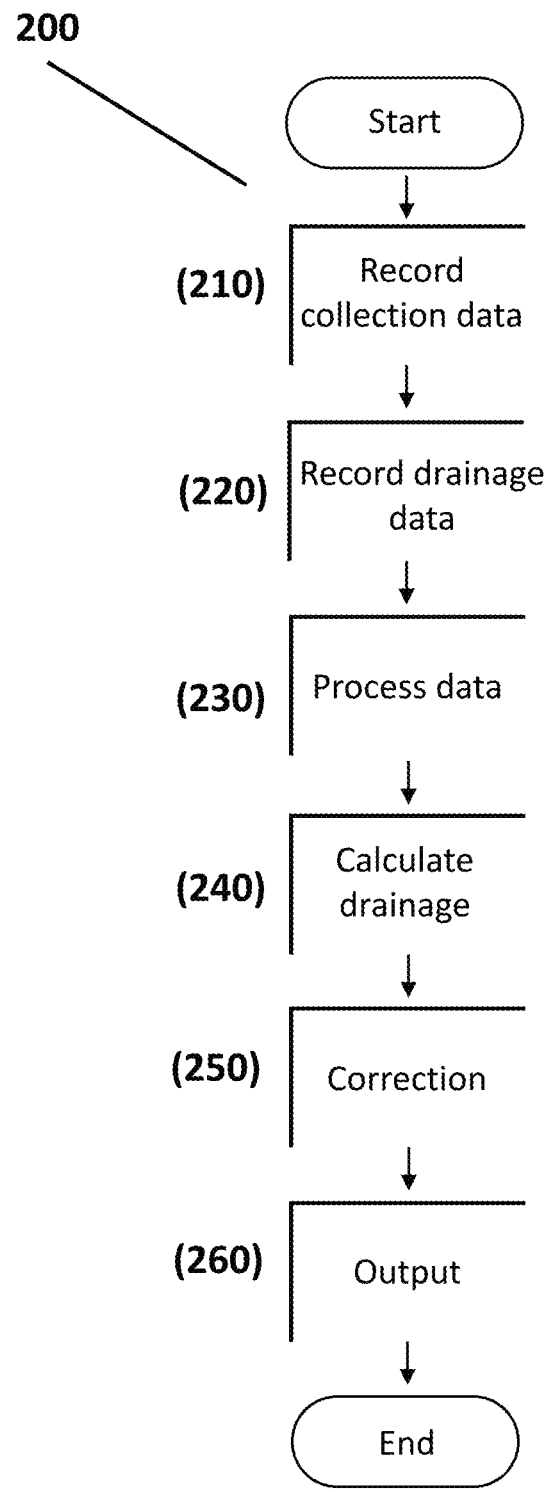
FIG. 2 shows a method performed according to an embodiment of the invention.

FIG. 2 shows a method 200 according to an embodiment of the invention. Some or all of method 200 is implemented while a subject is wearing or connected to the apparatus 100. The method 200 may be implemented by the apparatus 100 described above such as by computer-readable instructions being executed by the processor 111.

The method 200 may be initiated by user input or otherwise initiated by control unit 110. When the method 200 is initiated, the control unit 110 may be configured to begin processing the received BV and orientation signals, for example by storing them in the memory 112 or by performing dynamic analysis on the received signals i.e. on-the-fly analysis. Alternatively, the control unit 110 may be configured to store data corresponding to the signals during specific periods during the implementation of the method 200.

Figure 3:
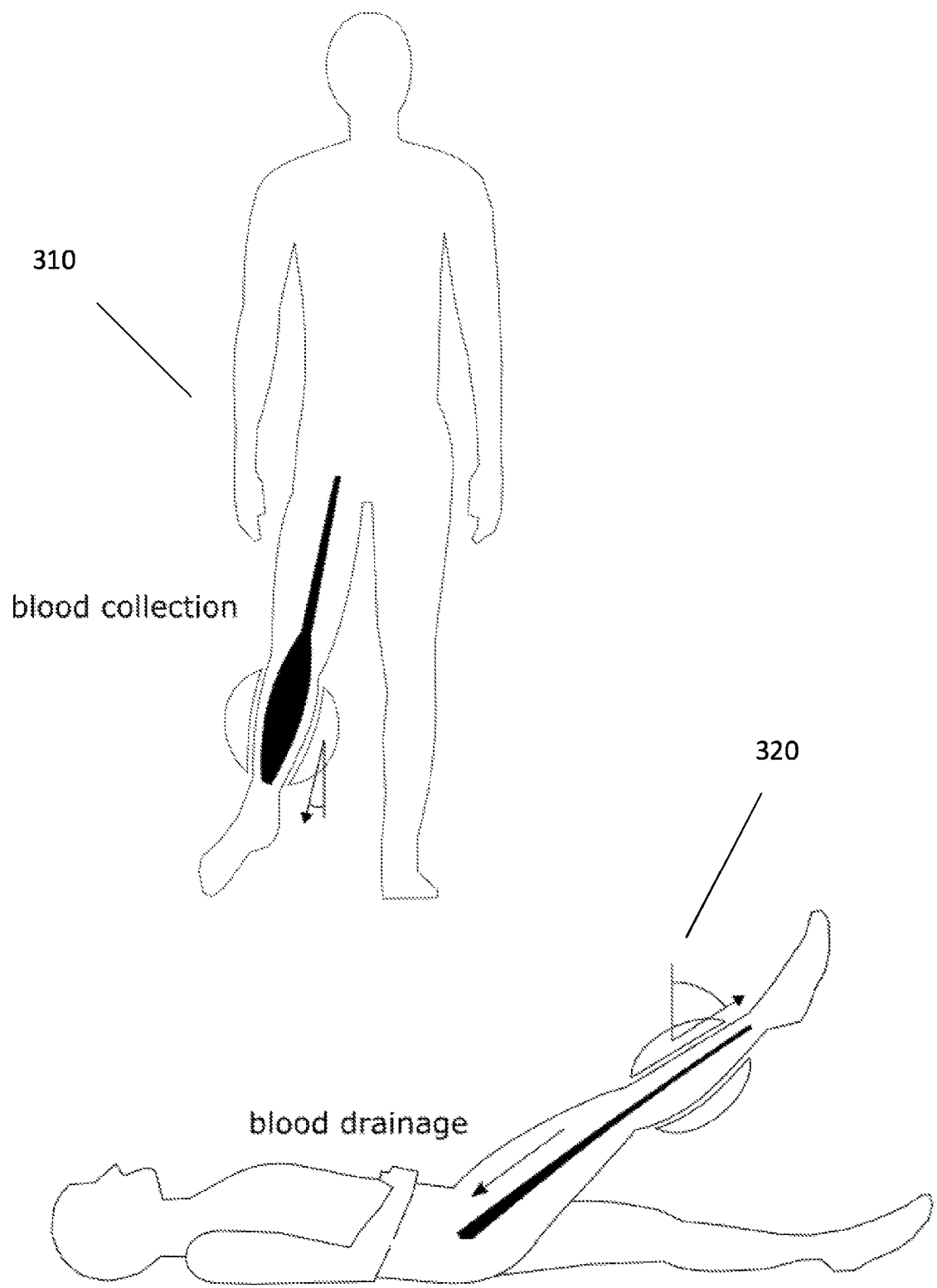
FIG. 3 shows an illustration of blood collection and drainage in a limb.

The method 200 may comprise an optional step 210 of recording collection data from the received BV and orientation signals. The data recorded in step 210 may correspond to a period of time in which the subject associated with the orientation sensor and BV measurement device is in a position facilitating the collection of blood within a limb. For example, if the limb is a leg, step 210 may comprise recording data indicative of the subject remaining in a standing position, optionally resting on the opposite leg. This position is illustrated in FIG. 3, as position 310. However, the subject may remain in any comfortable position during step 210, for example seated or supine. Step 210 may last a predetermined length of time to allow adequate blood collection, for example at least 30 seconds, at least 1 minute or around 1 minute, or until the control unit 110 determines that the blood collection has converged i.e. a change in blood volume has fallen below a predetermined rate, for example because the BV signal 145 has maintained a constant value. During step 210, the orientation sensor 130 outputs the orientation signal 135 indicative of an orientation of the limb, and the blood volume measurement device 140 outputs the BV signal 145 indicative of the blood volume in the limb. During step 210, the control unit 110 is configured to receive the BV signal and the orientation signal. The control unit 110 may be configured to store the data corresponding to the BV and orientation signals in the memory 112.

The method 200 may comprise a step 220 of recording drainage data. During step 220 the orientation sensor 130 and the blood measurement device 140 output the orientation signal and the BV signal. There may be no defined boundary by the control unit 110 between step 210 and step 220, but alternately there may be some user input to indicate to the control unit the transition between step 210 and step 220. Thus, in some embodiments, to initiate step 220 a user input may be received and the user interface 120. However in other embodiments the control unit 110 may be arranged to automatically determine when step 220 commences particularly from the orientation signal indicative of the change in orientation of the limb. During step 220, the subject raises the limb in a manner to facilitate blood drainage from the limb. An example subject position is illustrated in FIG. 3 as position 320, however other positions can be used. When the subject is in position 320, gravity facilitates the drainage of blood from the limb at which measurements are taken by the device 100. There will also be a transition period within step 220 during which the limb is in the process of changing position. During step 220, the control unit 110 is configured to receive the BV signal and the orientation signal. The control unit 110 may be configured to store the data corresponding to the BV and the orientation signals in the memory 112.

The method 200 may comprise a step 230 of processing the received data. Step 230 may be implemented by the control unit 110, which has been arranged to receive the BV signal and orientation signal from the blood volume measurement device and the orientation sensor throughout steps 210 and 220. The data contained in the received signals may be stored in memory 112.

Step 230 may comprise determining an orientation of the limb from the data corresponding to the orientation signal 135. As has been mentioned, apparatus 100 may comprise a plurality of orientation sensors, and control unit 110 may receive a plurality of orientation signals from the orientation sensors. Step 230 may then comprise determining a limb orientation in dependence on the data corresponding to the orientation signals 135.

Figure 4:
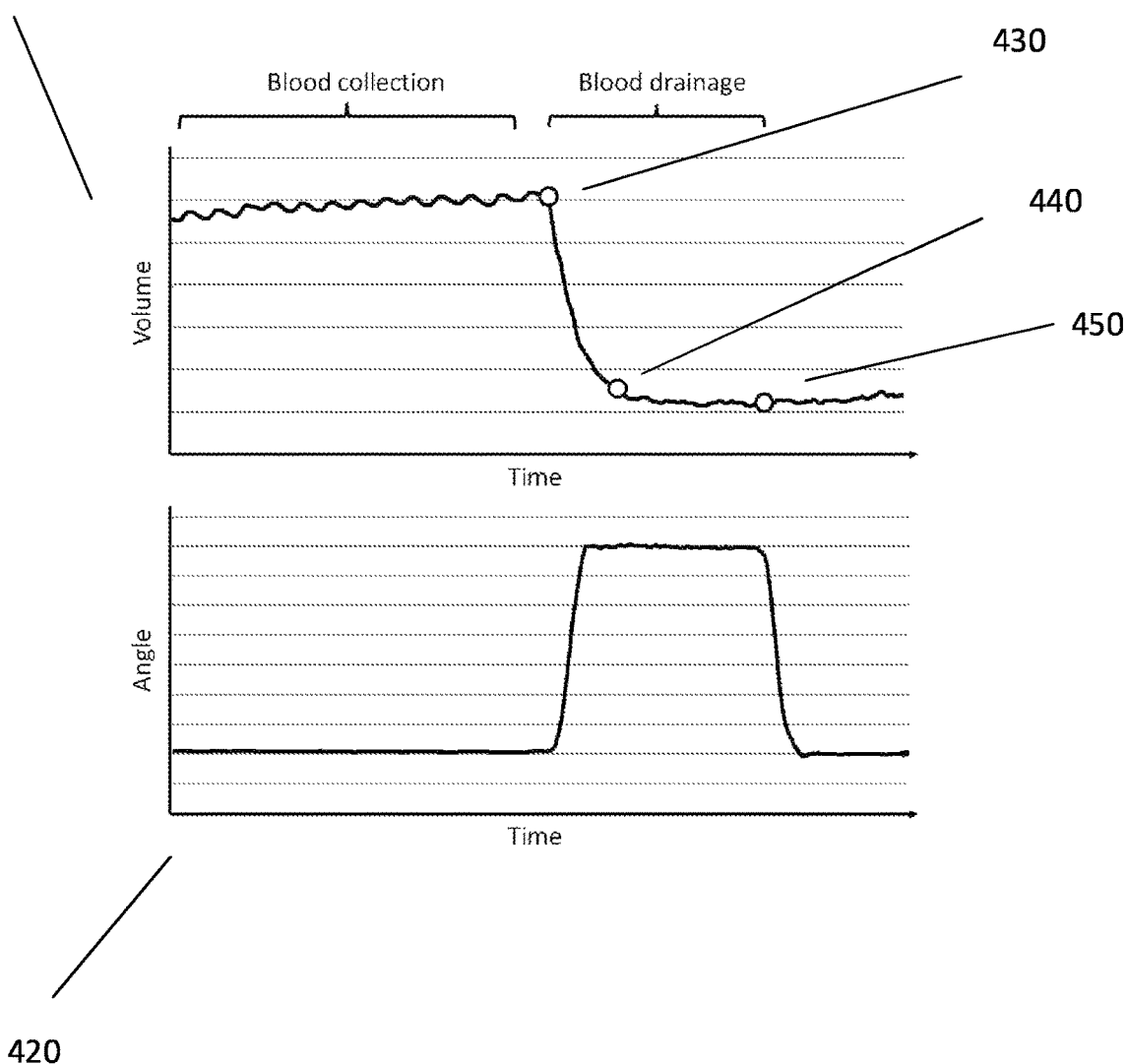
FIG. 4 shows a graphical representation of example blood volume and orientation data collected according to an embodiment of the invention.

FIG. 4 shows a graphical illustration of example data that may be stored in memory 112 as a result of step 220. Graph 410 illustrates blood volume against time, and graph 420 illustrates limb orientation, in this case leg angle, against time. Illustrated in FIG. 4 are two periods of time, 'blood collection' and 'blood drainage' which correspond to data collected during step 210 and step 220 respectively. As mentioned, these periods may be determined by user input. In some embodiments, these time periods may be determined in dependence on the limb orientation. For example, the time periods corresponding to steps 210 and 22 may be determined as the time for which the limb is in each orientation respectively.

In some embodiments, step 230 comprises determining a change in orientation of the limb in dependence on the limb orientation data, for example the orientation data represented in graph 420. The change in orientation of the limb may be indicative of the difference between the orientation of the limb during steps 210 and 220. For example, if the orientation data is a leg angle, step 230 may comprise determining a difference between a leg angle in the blood collection phase of step 210 and a leg angle in the blood drainage phase of step 220. However, in embodiments of the method 200 comprising only step 220, step 230 may comprise determining the orientation of the limb i.e. the leg angle during step 220.

Step 230 may further comprise determining a time associated with the change in orientation. For example, step 230 may comprise determining the time taken for the leg to change orientation between step 210 and step 220.

Step 230 may comprise determining a change in blood volume of the limb in dependence on the blood volume data, for example the blood volume data represented in graph 410. In some embodiments, the change in blood volume of the limb will be indicative of the difference between an initial blood volume level at the beginning of step 220 and a final blood volume level at the end of step 220.

Step 230 may comprise correlating the change in orientation with the change in blood volume of the limb. The correlation may comprise aligning the time associated with the change in orientation with the beginning of the change in blood volume. For example, the correlation may comprise associating time periods of the BV signal with steps 210 and 220 in dependence on the orientation signal.

Step 230 may comprise determining a drainage time of the limb in dependence on the BV data. The start of the drainage time may correspond to the start of step 220. In FIG. 4, the start of the drainage time is illustrated as point 430. The drainage time of the limb may be indicative of the time at which it takes the blood volume of the limb to drain to a predetermined level. For example, the drainage time may be the time taken for the blood volume to reach the final blood volume level, as illustrated in FIG. 4 as point 450. In other embodiments, the drainage time may be a time taken for the blood volume to have reduced by a predetermined portion of the change in blood volume, for example the time taken for the blood volume to have reduced by 90% of the total change in blood volume, as illustrated in FIG. 4 as point 440.

The method 200 comprises a step 240 of determining an indication of venous drainage of the limb. The indication of venous drainage of the limb may be determined in dependence on one or more of the change in orientation, the change in blood volume, and the drainage time of the limb.

In some embodiments, the indication of venous drainage of the limb is a Venous Drainage Index (VDI). The VDI is a ratio of blood volume to drainage time. In an illustrated embodiment, the VDI may be calculated as VDI=VDV/VDT, wherein VDV is the change in blood volume of the limb, and VDT is the drainage time of the limb.

In some embodiments the VDI may be calculated as a ratio of a pre-defined proportion of the total change in blood volume observed to a drainage time for the pre-defined proportion. For example, the VDI may be calculated as a ratio of 90% of the change in blood volume observed (90VDV) to the drainage time taken for the 90% change in blood volume to occur (VDT90). That is, in some embodiments, the VDI may be calculated as 90VDV/VDT90. It will be appreciated that the use of 90% is an illustrative embodiment and the use of alternative proportions may be envisaged in an analogous way.

Figure 5:
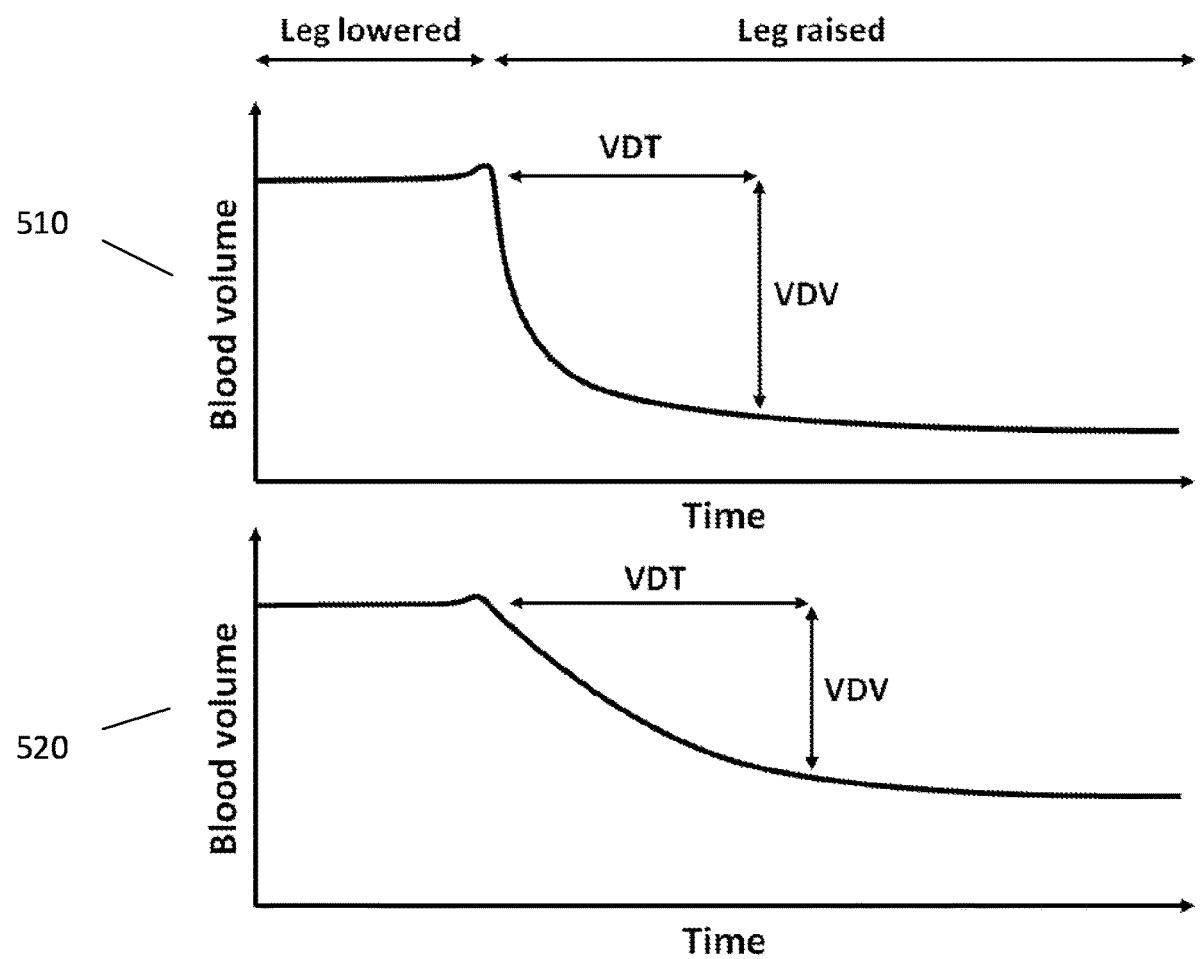
FIG. 5 shows a graphical illustration of example drainage time and change in blood volume.

FIG. 5 illustrates two sets of example blood volume data 510, 520. Time periods are marked in which the leg is lowered, and the leg is raised, corresponding to steps 210 and 220 respectively. These time periods may be extracted from the orientation data, as has been explained. An illustration of a change in blood volume (VDV) and a drainage time (VDT) is shown on each illustration of example data 510, 520. Example blood volume data 510 is illustrative of a leg with normal venous drainage, and example blood volume data 520 is illustrative of a leg with obstructed venous drainage. Advantageously, the venous drainage index (VDI) differentiates between the two cases. In a subject with obstructed venous drainage in the limb, a smaller amount of blood volume will be able to drain, and the drainage will take place more slowly. Consequently, the VDI will be reduced.

The method 200 may comprise a step 250 of correcting the indication of venous drainage. In some embodiments, step 250 comprises determining whether the data lies outside a predetermined boundary criteria. For example, step 250 may determine whether one or both of the change in orientation of the limb and the time taken for the leg to change orientation are within one or more predetermined boundary criteria. For example, the predetermined boundary criteria may comprise a minimum change in orientation. If the change in orientation is less than the minimum change, the data may be determined to be out of the predetermined boundary criteria. In some embodiments the predetermined boundary criteria may be a maximum time taken for the leg to change orientation, and if the time taken for the leg to change orientation exceeds this time, the data may be determined to be out of the predetermined boundary criteria. In a further example, the boundary criteria may comprise a minimum duration of step 220. If step 220 is determined to be shorter than the minimum duration, the data will be determined to be outside of the boundary criteria. These are illustrative examples of possible boundary criteria, although many others can be envisaged.

If the data is determined to be out of the predetermined boundary criteria, step 250 may comprise outputting an indication to the user, for example via user interface 120. This may act as an indication that new data needs to be collected.

In some embodiments, the data can be corrected if it lies outside the predetermined boundary criteria. In this case, step 250 comprises checking the data against predetermined correction criteria. If the data meets a predetermined correction criterion, step 250 may comprise applying a correction to the indication of venous drainage. The correction may be a predetermined value dependent on the predetermined correction criteria. For example, a plurality of correction values each associated with a predetermined correction criterion may be stored. For example, if the time taken for the leg to change orientation is within a range of values, there may be stored an associated correction value. For example, if the time taken is between 1-2 seconds outside the boundary criteria, one correction value may be applied. If the time taken is between 3-4 seconds outside the boundary criteria, a different correction value may be applied. These examples are only illustrative, and a variety of criteria can be envisaged. If the data fall within a predetermined correction criterion, step 250 may comprise retrieving the appropriate correction value and applying it to the indication of venous drainage. For example, the correction value may be added or subtracted from the indication of venous drainage to determine a corrected venous drainage value.

The method 200 may comprise a step 260 of outputting a drainage signal indicative of the venous drainage. The drainage signal may be indicative of one or more of the indication of venous drainage, the correction value, the correction criteria, and the corrected venous drainage value. The drainage signal may be output to the user interface 120 where it may be output to the user, for example as a visual or audio signal.

In some embodiments, step 260 comprises comparing the indication of venous drainage or the corrected venous drainage against a predetermined venous drainage value, and outputting a signal in dependence of the comparison. For example, the predetermined venous drainage value may be a threshold. If the indication of venous drainage falls below the threshold, step 260 may comprise outputting a signal indicating that the venous drainage falls below the threshold. The signal may be output to the user interface as a visual or audio indication. Advantageously, the predetermined venous drainage value may be indicative of normal drainage. In this way, step 260 can provide an indication to the user that the indication of venous drainage is normal or abnormal.

It will be appreciated that embodiments of the present invention can be realised in the form of hardware, software or a combination of hardware and software. Any such software may be stored in the form of volatile or non-volatile storage such as, for example, a storage device like a ROM, whether erasable or rewritable or not, or in the form of memory such as, for example, RAM, memory chips, device or integrated circuits or on an optically or magnetically readable medium such as, for example, a CD, DVD, magnetic disk or magnetic tape. It will be appreciated that the storage devices and storage media are embodiments of machine-readable storage that are suitable for storing a program or programs that, when executed, implement embodiments of the present invention. Accordingly, embodiments provide a program comprising code for implementing a system or method as claimed in any preceding claim and a machine readable storage storing such a program. Still further, embodiments of the present invention may be conveyed electronically via any medium such as a communication signal carried over a wired or wireless connection and embodiments suitably encompass the same.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed. The claims should not be construed to cover merely the foregoing embodiments, but also any embodiments which fall within the scope of the claims.

The invention claimed is:

1. An apparatus for determining an indication of blood flow in a limb, comprising:
 an orientation sensor for determining an orientation of the limb and outputting an orientation signal indicative thereof;
 blood volume measurement device for measuring an indication of blood volume (BV) in the limb and outputting a BV signal indicative thereof;
 a control unit arranged to receive the orientation signal and the BV signal, wherein the control unit is arranged to:
  determine a change in orientation of the limb in dependence on the orientation signal and to correlate the change in orientation with a change in blood volume of the limb determined in dependence on the BV signal;
  determine an indication of venous drainage of the limb in dependence on the correlation of the change in orientation with a change in blood volume of the limb; and
  determine a drainage time of the limb in dependence on the BV signal, indicative of the time at which it takes the blood volume of the limb to drain to a predetermined level.

2. The apparatus of claim 1, wherein the control unit is arranged to determine the indication of venous drainage of the limb in dependence on the drainage time of the limb and the change in orientation of the limb.

3. The apparatus of claim 2, wherein the indication of venous drainage of the limb is a Venous Drainage Index (VDI).

4. The apparatus of claim 3, wherein the control unit is arranged to determine the VDI as VDI=VDV/VDT, wherein VDV is the change in blood volume of the limb, and VDT is the drainage time of the limb.

5. The apparatus of claim 1, wherein the control unit is arranged to output a signal indicative of the indication of venous drainage.

6. The apparatus of claim 1, wherein the control unit is arranged to compare the indication of venous drainage against a predetermined venous drainage threshold and to output a signal in dependence on the comparison.

7. The apparatus of claim 1, wherein the control unit is arranged to determine whether the change in orientation of the limb is within one or more predetermined criteria.

8. The apparatus of claim 7, wherein the control unit is arranged to output an indication if the change in orientation of the limb is outside of the one or more predetermined criteria.

9. The apparatus of claim 7, wherein the control unit is arranged to correct the indication of venous drainage if the change in orientation of the limb is outside of the one or more predetermined criteria.

10. The apparatus of claim 1, wherein the blood volume measurement device is a pressure cuff.

11. The apparatus of claim 1, wherein the blood volume measurement device is one of an impedance measurement device, or a strain gauge.

12. The apparatus of claim 1, wherein the orientation sensor is one or both of an accelerometer and a gyroscope.

13. The apparatus of claim 1 comprising a plurality of orientation sensors each arranged to output an orientation signal;
wherein the control means is arranged to, in dependence on the orientation signals, determine an orientation of the limb.

14. The apparatus of claim 1, wherein the orientation signal is indicative of the orientation of the limb at predetermined intervals; and the BV signal is indicative of the blood volume in the limb at predetermined intervals.

15. A computer-implemented method for determining an indication of blood flow in a limb, comprising:
receiving, from an orientation sensor, an orientation signal indicative of an orientation of the limb;
receiving, from a blood volume measuring device, a blood volume (BV) signal indicative of a blood volume in the limb;
determining, in dependence on the orientation signal, a change in orientation of the limb;
determining, in dependence on the BV signal, a change in blood volume of the limb;
correlating the change in orientation with the change in blood volume of the limb;
determining an indication of venous drainage of the limb in dependence on the correlation of the change in orientation with a change in blood volume of the limb; and
determining a drainage time of the limb in dependence on the BV signal, indicative of the time at which it takes the blood volume of the limb to drain to a predetermined level.

16. The method of claim 15, comprising determining the indication of venous drainage of the limb in dependence on the drainage time of the limb and the change in orientation of the limb.

17. The method of claim 15, further comprising outputting a signal indicative of the indication of venous drainage.

18. The method of claim 15, further comprising comparing the indication of venous drainage against a predetermined venous drainage threshold and outputting a signal in dependence on the comparison.

19. The method of claim 15, further comprising determining whether the change in orientation of the limb is within one or more predetermined criteria.

20. The method of claim 19, further comprising outputting an indication if the change in orientation of the limb is outside of the one or more predetermined criteria.

21. A computer-readable data storage medium storing computer-readable instructions which, when executed by one or more processors, perform a method comprising steps of:
receiving, from an orientation sensor, an orientation signal indicative of an orientation of the limb;
receiving, from a blood volume measuring device, a blood volume (BV) signal indicative of a blood volume in the limb;
determining, in dependence on the orientation signal, a change in orientation of the limb;
determining, in dependence on the BV signal, a change in blood volume of the limb;
correlating the change in orientation with the change in blood volume of the limb;
determining an indication of venous drainage of the limb in dependence on the correlation of the change in orientation with a change in blood volume of the limb; and
determining a drainage time of the limb in dependence on the BV signal, indicative of the time at which it takes the blood volume of the limb to drain to a predetermined level.

* * * * *